(12) United States Patent
Brormann

(10) Patent No.: US 12,233,011 B2
(45) Date of Patent: Feb. 25, 2025

(54) RADIOLOGY HOLDING UNIT FOR A RADIOLOGY DEVICE

(71) Applicant: Febromed GmbH & Co. KG, Oelde (DE)

(72) Inventor: Hubert Brormann, Oelde (DE)

(73) Assignee: Febromed GmbH & Co. KG, Oelde (DE)

( * ) Notice: Subject to any disclaimer, the term of this patent is extended or adjusted under 35 U.S.C. 154(b) by 577 days.

(21) Appl. No.: 17/625,758

(22) PCT Filed: Jul. 13, 2020

(86) PCT No.: PCT/EP2020/069791
§ 371 (c)(1),
(2) Date: Jan. 9, 2022

(87) PCT Pub. No.: WO2021/009138
PCT Pub. Date: Jan. 21, 2021

(65) Prior Publication Data
US 2022/0240873 A1 Aug. 4, 2022

(30) Foreign Application Priority Data
Jul. 12, 2019 (DE) ............ 10 2019 119 025.8

(51) Int. Cl.
*A61G 7/10* (2006.01)
*A61B 5/055* (2006.01)
*A61G 7/053* (2006.01)

(52) U.S. Cl.
CPC ........... *A61G 7/1017* (2013.01); *A61G 7/053* (2013.01); *A61B 5/055* (2013.01); *A61B 2560/06* (2013.01)

(58) Field of Classification Search
None
See application file for complete search history.

(56) References Cited

U.S. PATENT DOCUMENTS 2,057,811 A * 10/1936 Armstrong ........... A61G 7/0533
482/904
5,836,026 A 11/1998 Reed
(Continued)

FOREIGN PATENT DOCUMENTS

CA 2228860 A1 * 10/1999 ........... A61G 7/1007
CN 201997042 U 10/2011
(Continued)

OTHER PUBLICATIONS

Translation of CA 2228860 A1 (Year: 1999).*
(Continued)

*Primary Examiner* — Thomas R Artman
(74) *Attorney, Agent, or Firm* — R. Dabney Eastham

(57) ABSTRACT

A radiology holding device (1) for a radiology apparatus (50) such as an X-ray apparatus (51), a magnetic resonance tomography apparatus (52), a computerized tomography apparatus (53) or a radiotherapy apparatus (54), comprising an attachment device (2) and pivotally accommodated thereon, a supporting arm (3) having at least one axle component (4) pivotally accommodated on the attachment device and a supporting component (5). Furthermore, a locking device (6) is provided for locking the supporting arm (3) in at least one locking position (7). An actuating mechanism (8) serves to actuate the locking device. A holding device (9) attached to the supporting arm (3) provides a patient with a holding means. The actuating mechanism (8) comprises a transfer component (11) passing through a hollow section (10) of the axle component (4).

32 Claims, 6 Drawing Sheets

(56) References Cited

U.S. PATENT DOCUMENTS

Figure 1:
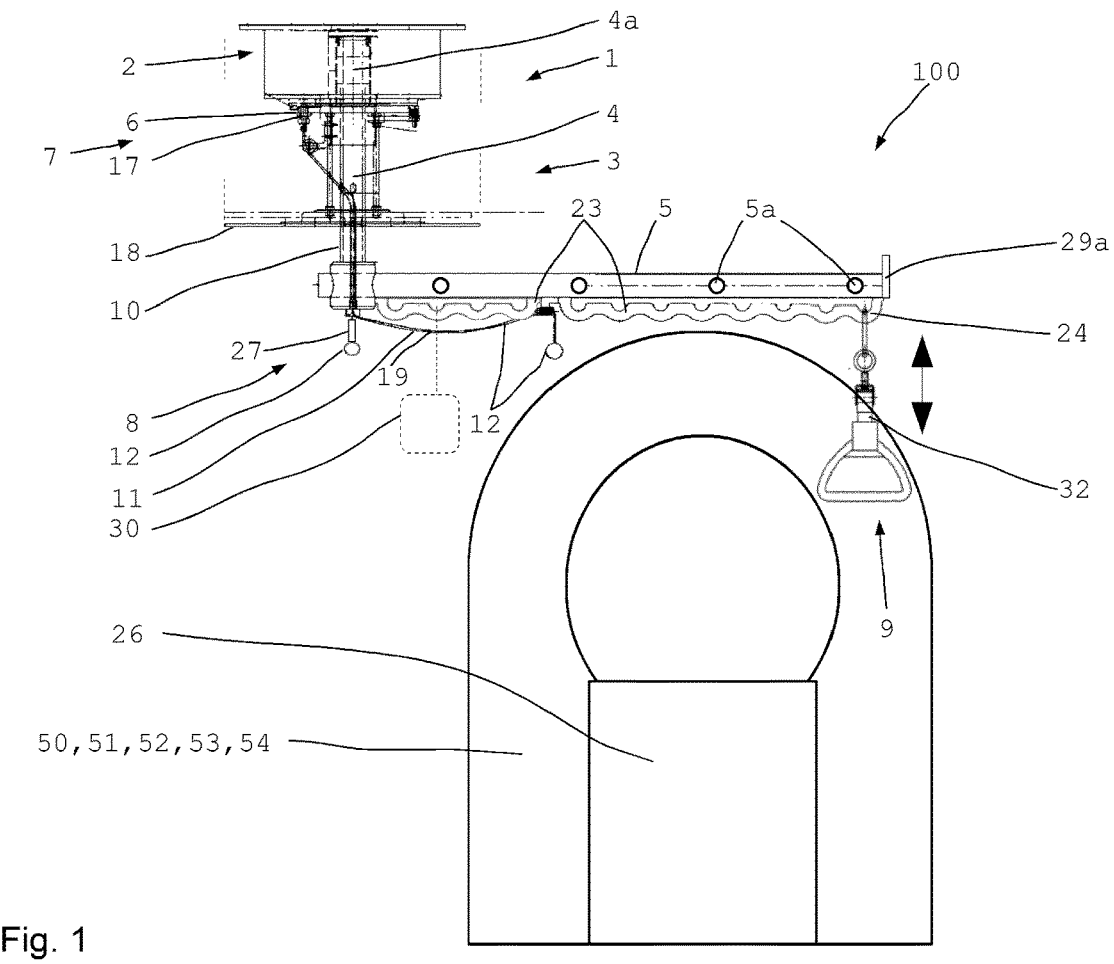

| | | | |
|---|---|---|---|
| 6,068,225 A | | 5/2000 | O'Brien et al. |
| 2006/0162083 A1* | | 7/2006 | Heimbrock ............ A61G 7/001 5/81.1 R |
| 2011/0239367 A1* | | 10/2011 | Gramkow ............ A61G 7/1015 5/81.1 R |
| 2022/0240873 A1* | | 8/2022 | Brormann .............. A61B 5/055 |
| 2023/0270393 A1* | | 8/2023 | Brormann ............ A61G 7/0536 378/20 |

FOREIGN PATENT DOCUMENTS

| | | | | |
|---|---|---|---|---|
| CN | 204274741 U | | 4/2015 | |
| CN | 105664436 B | * | 12/2017 | |
| DE | 29709508 U1 | * | 8/1997 | ............ A61G 7/053 |
| DE | 202016106093 U1 | | 3/2018 | |
| DE | 202019103864 U1 | * | 11/2020 | |
| EP | 0610664 B1 | * | 4/1997 | |

OTHER PUBLICATIONS

Translation of CN 105664436 B (Year: 2017).*
Translation of DE 202019103864 U (Year: 2020).*
Translation of EP 0610664 B1 (Year: 1997).*
Canadian Intellectual Property Office (CIPO) office action and search report issued on Nov. 8, 2023 for the Canadian application 3,142,563 that was filed on Dec. 2, 2021.
Claims filed on Dec. 2, 2021 in Canadian application 3,142,563, as downloaded from the CIPO website.
International Search Report issued for PCT/EP2020/069791.

* cited by examiner

RADIOLOGY HOLDING UNIT FOR A RADIOLOGY DEVICE

The present invention relates to a radiology holding device, in particular for a radiology apparatus, and to a radiology system having such a radiology holding device and a radiology apparatus, such as in particular a computer tomograph (CT), magnetic resonance tomograph (MRT), X-ray apparatus, radiotherapy apparatus or the like.

Computer tomographs or magnetic resonance tomographs tend to include a kind of tube, through which the patient is pushed or passed for taking the required images. Hereinafter, magnetic resonance tomographs or computer tomographs will be generally referred to by the term X-ray apparatus. In the case of a bedridden patient to be subjected to X-ray or MRT- or CT-imaging by means of such an X-ray apparatus, the bedridden patient, lying in a bed or sitting in a wheelchair, is pushed into the room equipped with the X-ray apparatus, and positioned next to the stretcher or the treatment table. Then, the patient must be transferred from the bed or the wheelchair or the stretcher onto the treatment table, prior to starting the MRT- or CT process. These transfers and correct positioning require much force and time.

DE 20 2016 106 093 U1 has disclosed such a radiology holding device with which to support and assist in these actions. An adjustable supporting arm includes a holding grip for a patient to hold on to. The supporting arm angle can be fixed. Pulling a cable releases a bolt from a hole circle so as to enable rotating the entire supporting arm. A drawback is the large space required since the entire hole circle must be passed through an intermediate ceiling. This means a large-area penetration of a magnetic sealing disposed in the intermediate ceiling. Thus, e.g. magnetic shielding will be considerably more complicated. The cable for releasing the bolt rotates jointly with the supporting arm. In many positions, reaching the cable is suboptimal for staff of small size or short arm span. Although motorized adjusting and angle fixation is basically feasible, it requires a very powerful electric motor which can apply a sufficient rotational force already in standstill so as to prevent unintentional rotations of the supporting arm in operation. The complexity required is considerable.

It is therefore the object of the present invention to provide an improved radiology holding device, with which to allow employment in radiology involving reduced complexity and with which to achieve support and assistance for patients and operators.

This object is solved by a radiology holding device having the features of claim 1 and by a radiology system having the features of claim 31. Preferred specific embodiments of the invention are the subjects of the subclaims. Further advantages and features of the present invention can be taken from the general description and the description of the exemplary embodiments.

A radiology holding device according to the invention is in particular provided for at least one radiology apparatus and preferably for at least one X-ray apparatus, MRT apparatus or CT apparatus, or radiotherapy apparatus or similar or comparable apparatus. The radiology holding device comprises an attachment device and at least one supporting arm pivotally accommodated thereon. The supporting arm comprises at least one axle component and at least one supporting component. The radiology holding device comprises at least one locking device for locking the supporting arm in at least one angular position. The angular position in which the supporting arm can be locked, is a locking position.

At least one actuating mechanism is provided to actuate, and in particular release and/or lock, the locking device. At least one holding device is provided for attachment to the supporting arm, for example to provide a holding means for a patient. Thus, the patient can for example grip the holding device which assists in pulling himself up, transferring, repositioning, or shifting himself. The axle component of the (one or more) supporting arm(s) is pivotally received, and in particular supported, on the attachment device. This allows ease of pivoting the supporting arm to enable different working positions. The actuating mechanism comprises at least one transfer component which passes through at least one hollow section of the axle component.

The radiology holding device according to the invention is very advantageous. A considerable advantage is, greater ease of handling. Even short persons experience ease of operation. A considerable advantage is improvement of hygiene, since the transfer component is passed through the hollow axle and is thus subjected to reduced risk of contamination.

In proper, normally installed respectively ready-to-use state as intended, a rotation axis is at least substantially oriented in the vertical or approximately vertical or (nearly or exactly) vertical or inclined. The attachment device is preferably configured as an attachment console which is in particular attached to the room ceiling e.g. of a radiology department.

In other configurations, the attachment device may in particular also be configured as a wall mounting which is supported on a room wall that is e.g. substantially vertical.

The holding device is in particular configured as, or comprises, a holding grip. The holding device (respectively the holding grip) is in particular height-adjustable and thus can be adapted to shorter and longer persons. Preferably, the holding device or at least one holding grip is height-adjustable by at least 100 mm and in particular by 200 or 300 mm, or 500 mm or more, e.g. even 1 m or more.

The supporting component respectively its bottom face is preferably disposed at a height of 2250 mm or more. The holding device can preferably be disposed at a height of 2000 mm or more.

The attachment device can also be disposed directly on the radiology apparatus and/or can in particular be integrated therein and/or attached thereto. In this and in other cases, the orientation of the supporting arm rotation axis can be adjustable by adapter. Alternately, the actuating device can be attached to a wall or on the floor.

The supporting arm is disposed and/or accommodated and preferably fastened, preferably rotatably, in particular at least pivotally, at least to the attachment device of the radiology holding device. The transfer component moves, in particular at least in sections, substantially axially along the rotation axis or closely adjacent to the rotation axis, when the actuating mechanism is actuated. Preferably, the transfer component moves in the region of the axle component, at least in sections, through the axle component which is in particular hollow.

Due to the transfer component passing through the hollow section of the axle component, the radiology holding device in its entirety, and in particular the supporting arm, is particularly compact and space-saving. The transfer component does not need to rotate along around a rotation axis of the supporting arm while the supporting arm is pivoting. Consequently, passage through magnetic shielding is particularly easy. Passing the transfer component pivotally through a shielding, if any, or partition wall, does not require any slot, elongated hole, or linear aperture. The sealing respectively shielding is considerably easier and simpler.

In the case of a conceivable passage of the radiology holding device through a suspended ceiling, for example with magnetic shielding (Faraday cage), the surface of passage is limited to the cross-sectional area of the axle component. Thus, the shielding needs only be opened and/or broken over a minimal cross section. In any case, sealing the hole in the shielding is less complicated or optionally not required at all.

The transfer component is preferably made of a non-magnetic and/or an electrically non-conducting material. This avoids an antenna effect by means of the transfer component. This applies in particular in the region of the passage through the axle component, and in particular through the shielding and into the immediately adjacent regions or in the immediate vicinity.

An axle component and/or a supporting component is/are preferably configured, at least partially and/or in sections, along the respective longitudinal axis, as a (circumferentially closed) tube section showing a cross section that is, at least partially and/or in sections, circular and/or oval and/or square. The cross section may be in particular round, triangular, quadrangular or polygonal. Also, an axle component and/or a supporting component may be configured as an open U-profile and/or V-profile, at least in sections and/or at least partially. The partial configuration as a tube section and/or open profile offers a very sturdy and torsionally rigid construction. It allows good force introduction and force transmission, and a simple and robust structure.

The axle component and/or the supporting component are particularly preferably manufactured of a stainless metallic material, in particular "VA steel" or another stainless steel alloy. In particular is the material surface configured so that paint coating can be dispensed with. Thus, paint or paint particles are prevented from peeling off and/or scaling off and/or abrading due to mechanical loads and stresses, which would cause contamination. Conceivable contamination is minimized and/or never occurs due to hard or hardened surfaces and due to eliminating cracking.

The radiology holding device can in particular be subjected to loads of at least 1350 N or at least 1500 N or 1700 N or 2000 N, preferably in the direction of the gravitational force. In a heavy-load configuration, the radiology holding device can preferably be subjected to loads of up to 5000 N.

The radiology holding device in particular supports load moments of at least 5.5 kNm or at least 6.5 kNm or, in a heavy-load configuration, at least 10.0 kNm. The radiology holding device may preferably be configured for supporting lower or higher forces and/or load moments. This is above all dependent on the loads expected. In the case that primarily, or only, children are to be shifted, the load limit may be configured considerably lower. For special radiology systems for highly overweight persons, the radiology holding device may be configured for considerably higher loads.

It is particularly preferred for the actuating mechanism of the radiology holding device to be operated by at least one actuating member. An actuating member may particularly preferably be configured as a button and/or knob and/or handle. Alternately it is possible to form an actuating member by a cable loop and/or cable end. Other geometric shapes or bodies are conceivable as well.

The actuating member can be disposed immediately centrally and centered beneath the supporting arm, in particular by passing the transfer component through the hollow axle component. Thus, users can actuate the actuating mechanism centrally from many positions, for pivoting the supporting arm via the actuating member and the transfer component. In this case, the position of the actuating member is hardly, or not at all, changed by pivoting the supporting arm. This enables a reduced distance of the actuating member from the radially outwardly end of the supporting arm. This facilitates operating and pivoting in particular for short persons, if the operating position shows a radially long distance from the rotation axis.

The actuating member may also be configured as an electric sensor and/or switch. In this case, the locking device is actuated electrically via the actuating mechanism.

Preferably, the actuating mechanism can be operated by way of at least two (in particular mechanical) actuating members which are independent of one another. In simple cases, at least one part or section of a transfer component can be formed by a cable or yarn or the like.

In particular, more than two actuating members are provided by which the actuating mechanism can be actuated separately. In particular, the two or at least two actuating members are disposed at different radial distances from the central pivot or rotation axis of the supporting arm. At least two actuating members each can be disposed on, respectively connected with, the transfer component in series and/or parallel switch. The actuating members can be oriented such that actuation is advantageously feasible from different positions on the supporting arm. Also, an actuating member may be formed by the transfer component itself. To this end, an actuating member may be formed by an approximately horizontal section of the transfer component.

Particularly preferably, at least one actuating member, which can actuate the locking device, is disposed and/or attached radially outwardly of the attachment device. Advantageously, an actuating member is in particular disposed immediately adjacent to at least one holding device. A holding device may preferably be disposed in the vicinity of, or at, the radial end, i.e. given a large supporting arm radius. Advantageously, actuation may be done from the vicinity of a holding device. Optionally even by the patient, if safety is not significantly jeopardized. Furthermore, simple actuation may be performed by at least one assisting person. Then, an operator can e.g. pull the actuating member, thus pulling the transfer component configured e.g. as a cable, thus releasing the locking device, and simultaneously with actuating, can pivot the supporting arm to a desired position.

Preferably, the locking device of the radiology holding device establishes a force-fit and/or form-fit connection between the supporting arm and the attachment device. The locking device can in particular be configured in a force fit as a friction brake and/or belt brake or the like, where the locking position is implemented in a force fit due to the interaction of friction linings and/or a belt on the accommodation. Preferably, a friction lining is accommodated or configured (e.g. integrally) on the accommodation, and a friction lining, on the supporting arm. In this case the supporting arm is non-rotatably clamped respectively locked in a locking position. Alternately, the locking position can be implemented in a force fit e.g. by means of a magnetically acting locking device. In this embodiment, the locking device of the supporting arm is retained in the desired locking position e.g. either directly by magnetic forces, or magnetic forces are utilized for transferring a fixing member to, and/or retaining it in, a locking position. In these cases, any desired locking position is feasible in any desired angular position.

Particularly preferably, however, the locking device can be designed in a form fit. In this case, the angular position is locked by means of interlocking, form-fit members. It is possible to configure the form-fit connection by way of interlocking members, or by toothing, or another form-fit contour layout.

Advantageously, the locking device comprises at least one fixing member for locking the locking device. Preferably, the transfer component can be transferred from a locking position to a rotary position, in which the angular position of the supporting arm can be varied relative to the attachment device. In particular, the supporting arm is freely rotatable, or pivotable in a predefined angular range, in the rotary position. Particularly preferably, (fixed) grid points are provided.

The transfer component is connected with the fixing member (indirectly and/or directly, in a force fit and/or form fit). Alternately, the transfer component may be configured as, or at least comprise, an electric conductor and/or actuator. In this and in other cases, at least one additional actuator or actuating device may be comprised. For example, a positioning motor may be provided, by means of which the fixing member can be transferred from the locking position to the rotary position (and reversely).

It is possible for the radiology holding device to be pivoted and/or rotated by at least one actuating device and in particular by a motor and preferably an electric motor. In this case, the radiology holding device can be pivoted in particular by remote control provided with a wireless or wire-bound connection with the actuating device. In this case, the radiology holding device can in preferred variants be pivoted solely by the actuating device while it is locked in a secure locking position. Such a safety function can preferably be overridden by at least one safety switch. Actuating such a switch allows pivoting the radiology holding device even if the radiology holding device is not in a locking position.

The actuator used is preferably not motor- or electrically driven. In all the configurations, the locking device preferably comprises at least one fixing member meshing with at least one of a plurality of click-in elements. A fixing member is in particular configured and/or disposed on the attachment device, so as to enable multiple locking positions for fixing.

A click-in element is in particular configured as a depression, and preferably as a hole or bore. At least one fixing member is in particular configured as an engagement component allowing, or establishing, a form-fit connection with the attachment device. At least one engagement component is advantageously configured as a bolt, engaging in a form-fit, in a locking position with an adapted hole in the attachment device.

A click-in element and a fixing member preferably interact so as to enable the locking position. When the click-in element and a fixing member are engaged with one another, rotation is blocked, and when disengaged, the supporting arm can be pivoted. Particularly preferably, a click-in element is configured as a depression, and the fixing member comprises a bolt or the like for insertion into the depression. Reverse action is also conceivable, where the fixing member e.g. shows a depression into which the click-in element, which is e.g. bolt-shaped, engages in the locking position. It is also possible for the fixing member and the click-in element to be configured as adapted, preformed parts interlocking in a form-fit (and/or also force-fit).

The fixing member as a component of the locking device is preferably disposed on the supporting arm. A plurality of depressions is preferably configured and/or disposed on the attachment device.

Alternately, the bolts and the depressions can be paired exactly opposite the supporting arm and the attachment device, if it appears required or desired due to the structure.

The configuration of the locking device by means of at least one bolt as a fixing member respectively an engagement component engaging in a hole of a hole circle offers the advantage that manufacturing the locking device is particularly simple and inexpensive. The structure is very sturdy. The form-fit connection is good for absorbing transverse forces and torques, and for reliably fixing the supporting arm in a locking position. The mechanism can be disposed centrally and space-savingly around the rotation axis of the supporting arm.

Particularly preferably, a plurality of depressions and in particular holes and/or bores are distributed over the circumference on a disk or e.g. a ring, in particular as a (periodical, even) hole circle disposed on the attachment device. Pivoting the supporting arm allows to fix the bolt of the supporting arm in various angular positions, in that the bolt engages in one of the holes distributed over the circumference of the hole circle. In this way, the supporting arm can be fixed in the desired locking position.

Particularly preferably, the bores are disposed equidistantly at a pitch of preferably 5°, 10°, 15°, and/or in particular 30°, and/or particularly preferably 45°, and/or in particular 90° to one another. Other pitches are likewise conceivable. It is furthermore possible for the bores to be distributed over the circumference at a non-even pitch. For example, a plurality of depressions may be given on a small circumferential section, while just a small quantity of possible locking positions is disposed on another, corresponding circumferential section.

In an advantageous configuration variant, the depressions are disposed (approximately in a circle) across a diameter that is larger than the diameter of the axle component. Particularly preferably, the depressions are disposed in a circle across a diameter that is larger than 1.5 times or twice the (outer) diameter of the axle component. This is advantageous for particular ease of implementing the engagement of a bolt in a depression. The locking device with the depressions disposed in a circle, and a fixing member configured as a bolt, cone, cone frustum, or the like, are particularly easily accessible. This is an advantage primarily in maintenance and repair work. Thus, the locking device can preferably be disposed immediately adjacent to the axle component.

Preferably, the radiology holding device comprises at least one biasing device which can bias the engagement component in the locking position. The biasing device particularly preferably causes the locking device to be in the locking position, regularly or (nearly) at all times, unless the actuating mechanism puts it in the rotary position. Biasing is in particular feasible by at least one biasing spring, which urges the bolt as the fixing member at suitable angular positions into the hole of the pertaining locking position. The biasing device may preferably be configured as, or at least comprise, a compression spring, coil spring, helical spring, leaf spring, or other resilient member. It is also possible to utilize the resilient properties of another component for biasing the fixing member. The biasing device may in particular be configured as a magnetic or pneumatic mechanism.

In the case of movement in the rotary position, the biasing device preferably locks the fixing member in position automatically when the fixing member engages in a depression during the rotary motion. In this way, the supporting arm is advantageously regularly, or always, biased to a fixed, angular position.

Due to biasing the fixing member in the locking position, the supporting arm of the radiology holding device is non-rotatably locked in its angular position respectively in the locking position. A person can safely pull him/herself up, and/or support him/herself, on the holding device of the radiology apparatus, so that the radiology holding device can be non-rotatably utilized for shifting a person. In the case of shocks and/or jerky movements of any component of the radiology holding device, the angular position of the supporting arm is reliably locked, and cannot even be moved by impulses.

Preferably, the axle component shows, at least in a medium range along the longitudinal axis, a shield or a cover device extending in particular transverse and preferably perpendicular to the axle component. The shield serves in particular to cover or seal a passage through at least one intermediate ceiling and/or a magnetic shielding. In and/or on an intermediate ceiling, magnetic shielding is in particular provided which sufficiently shields radiation emitted from an operating radiology apparatus. The shield in particular closes the magnetic shielding, so as to enable safe and reliable operation of a radiology apparatus. To this end, appropriate materials for shielding can be in particular worked and/or incorporated into and/or on the shield. A connection of the shield with at least one intermediate ceiling may potentially make it suitable to additionally support the axle component. This improves the system rigidity. A number of shields may be disposed on an axle component.

A configuration without a shield is likewise possible. This configuration variant is particularly preferred if the radiology holding device is intended for a room without any intermediate ceiling and/or on a wall. An additional covering device may be provided, which completely covers in particular the attachment device and the locking mechanism.

Particularly preferably, the transfer component comprises at least one flexible pull member. The flexible pull member is in particular configured as, or comprises at least one, cable or pull rope, band, yarn, rubber band and/or chain. The transfer component is in particular configured as a flexible pull member. The transfer component may be configured multipart. At least one component may be configured as, or comprise, a rigid rod.

The actuating member may in particular be provided with an additional protective sleeve, which protects the transfer component and the actuating mechanism from contamination, primarily from the user's hands. The protective sleeve is particularly preferably configured in a cylindrical and/or annular shape. Other configurations are likewise conceivable. Preferably, the sleeve may simply surround the transfer component. In the case that an adjacent actuating member is configured as a knob, it can readily support the sleeve so that the sleeve positions itself by gravity. The sleeve is particularly preferably manufactured of a material or material combination showing an antibacterial finish and providing for easy cleaning. The material advantageously shows a smooth surface so that no dirt can settle. Preferably, the protective sleeve has a length greater than 5 mm and in particular greater than 10 mm. Preferably, the protective sleeve is configured in a length between 5 mm and 100 mm, in particular between 10 mm and 60 mm. The protective sleeve in particular immediately follows an actuating member.

In a particularly advantageous variant, the transfer component is passed out of the interior of the axle component to a region radially outwardly of the axle component. Then the transfer component is passed (particularly space-saving) through the axle component. Thus, the transfer component does not need to be passed separately adjacent to the axle component, through an opening in the intermediate ceiling, which must be sealed separately, as in the prior art. The opening required is thus limited to the axle component and its cross section. The transfer component does not need to rotate along around the axle component while the supporting arm is pivoting. The transfer component pivots substantially centrally with the axle component.

Particularly preferably, the transfer component is accommodated and/or guided on the supporting component over at least one quarter or at least half the length of the supporting component, in particular at least two thirds of the length of the supporting component, and/or advantageously at least three quarters of the length of the supporting component. This allows to position an actuating member particularly preferably (always) in the vicinity of a holding device, wherever the holding device is mounted. The actuating mechanism may optionally be provided for actuation by a patient. At any rate, it tends to be possible for an operator to pull the actuating member, releasing the locking device, while the same operator is guiding the supporting component of the supporting arm for pivoting. The radial distance of the actuating member from the guiding point for pivoting the supporting arm is considerably shorter than in the prior art. The actuation point and the pivot point are also disposed on the same radial side of the supporting arm, additionally facilitating operation.

Preferably, the transfer component is passed out of the axle component, through at least one guide unit inside of the axle component, and/or at least one time from the inside to the outside. The transfer component is particularly preferably passed inside of the axle component, through a guide unit which is configured as a guide rail. The guide rail is in particular configured as a tube section showing a circular and/or oval and/or polygonal cross section, having in particular three, four, five, and/or more angles.

Alternately, the guide unit may be configured as an open profile having a U-shaped and/or V-shaped cross section. The guide unit particularly preferably guides the transfer component over at least one section along the axial direction inside of the axle component. The guide unit causes the transfer component to pass at least one time radially outwardly from the inside, and/or at least one time radially inwardly from the outside.

The guide unit can be one-piece and/or multi-piece. It can consist of multiple materials. A side on which the transfer component is passed, may show a particularly friction-inhibiting surface and/or may be provided with a friction-inhibiting coating or layer, so as to facilitate and improve the movability of a transfer component, such as graphite. Also, self-lubricating coating by means of oil and/or grease may be provided.

The guide unit is advantageously configured of a plastic, offering a particularly smooth surface for the transfer component to glide over. Another side and/or position of the guide unit may comprise a material which is particularly suitable for suspending or otherwise mounting the guide unit inside of the axle component, such as steel.

A configuration of the transfer component as a mechanical pull member or cable, chain or band offers the advantage that a button and/or knob as an actuating member can be attached at its end, by means of which the actuating mechanism can be operated. Preferably, the actuating mechanism comprises at least one force direction unit. Advantageously, the force direction unit comprises at least one holding part, which in particular accommodates the flexible pull member. The actuating mechanism can be operated easily and directly. In operation, a flexible pull member can readily compensate for minor changes of position of an operator's hand, so that the actuating member traces the movements of the patient's and/or an operator's hand. The direction and/or the orientation and/or the local progression of the pull member can be disposed variably, to the advantage of the user, so that the cable end can also be directly used as an actuating member.

A configuration of the transfer component as a mechanical pull member offers the further advantage that at least two actuating members can readily be connected with the transfer component in series and/or in parallel. Thus, the actuating mechanism can advantageously be actuated by at least two actuating members. A flexible pull member of the transfer component can be, or is, likewise preferably installed along the supporting arm and in particular along the supporting component. The transfer component may be used itself as an actuating member. Various actuating members may be radially distanced from one another, so as to enable actuation from various positions along the supporting arm and in particular along the supporting component of the supporting arm.

Preferably, at least one force direction unit is comprised. The force direction unit allows to directly transmit to the locking device, an operating force introduced for actuating the locking device, and to utilize the operating force for actuating the locking device. A force direction unit preferably transmits the operating force applied to the actuating member in a preferred direction. This means that the transfer component is moved in a preferred direction. In the case that multiple actuating members are provided in different positions in series, and an actuating member in the middle is actuated, then the force direction unit causes introduction of the force substantially in one direction only. Movement of the transfer component substantially occurs in one direction. Movement in the opposite direction is largely prevented. This reduces the actuation travel required, since the force direction unit controls the direction of the force applied for actuating the locking device, effectively steering it in the desired direction.

The risk that, in particular when shifting a patient, the locking device may be inoperable or only operable involving a very long and/or undefined actuation travel, is minimized or even entirely eliminated.

The flexible pull member respectively the transfer component may be disposed at a great horizontal distance from the locking device. Even in the case of a long, horizontal guide of the flexible pull member, the proportion of the introduced tractive force or actuation travel not contributing to actuating the locking mechanism, is minimized.

Even in the case that the flexible pull member sags, and in the case of multiple pull members and/or actuating members connected in series or connected with one another, a defined, and invariable or always nearly identical actuation travel can be set.

Preferably, the actuation travel required for actuating between at least two or nearly all or all of the different actuating members, varies by less than 150 mm or 100 mm and preferably by less than 50 mm and particularly preferably less than 25 mm.

Preferably, the actuation travel required for actuating between at least two or nearly all or all of the different actuating members, varies by less than 300% or 200% and preferably by less than 100% and particularly preferably less than 50% or 25%. Shorter actuation travels may show larger percentage deviations than do longer actuation travels.

In a specific configuration, the actuation travel along a first actuating member is 15 mm and it may be longer or shorter by up to 10 mm, depending on the construction and settings. Then, the deviation from the actuation travel of a second actuating member or from the actuation travels of (nearly) all the other actuating members is in particular less than 50 mm and preferably less than 20 mm or preferably less than 200% of the actuation travel. However, if the normal actuation travel is already 100 mm, then the deviation from the actuation travel of a second actuating member is in particular less than 100 mm and preferably less than 50 mm.

The positions of the flexible pull member and the actuating member for actuation are preferably adjustable and adaptable. This noticeably facilitates the work for nurses or operators and increases patient comfort. Intuitive operation is possible, since the actuating member can be expected to be, and is, disposed substantially in the same position at all times.

On the whole, the operability of the radiology holding device and in particular of the supporting arm is improved. The reliability of the actuating mechanism is clearly improved. The defined positioning of the transfer component and the flexible pull member protects these from excessive contamination. The actuating member is advantageously always gripped at the same spot. This aids and promotes in particular the hygiene of the radiology holding device. Moreover, the actuating mechanism is primarily easier in handling. Use is facilitated.

In at least one advantageous specific embodiment, the actuating mechanism comprises at least two force direction units. Three, four, five, or still more force direction units can in particular be comprised.

Advantageously, one or at least one force direction unit per actuating member is comprised. Moreover, it can be advantageous to provide, in the case of a long pull member or transfer component, one, two or more force direction units to ensure reliability in actuating the locking device. Advantageously, multiple force direction units prevent respectively compensate for unintended sagging, or stretching, of the transfer component and in particular of the pull member. This enables, and still further improves, reliability of actuation with a substantially defined actuation travel.

Preferably, the actuation travel of the pull member is less than twice the diameter of the actuating member. Advantageously, the actuation travel can be at least less than four times, eight times, or even twenty times the diameter of the actuating member. In at least one advantageous specific embodiment, the actuation travel substantially corresponds to the minimally required travel for the actuation of the actuating mechanism of the locking device. The stroke length respectively the actuation travel of the transfer component is preferably and/or maximally 5 mm, and in particular between 10 mm and 20 mm, and preferably approximately 15 mm. Moreover, the actuation travel may be up to 30 mm, 60 mm, and even up to 120 mm or still more. Advantageously, a short, defined actuation travel can improve the handling of the radiology holding device. Users do no longer need to assume an undefined actuation travel. Thus, accidents can advantageously also be prevented.

Advantageously, the force direction unit comprises at least one holding part. Preferably, the force direction unit comprises at least one support part. The support part is preferably disposed on, and particularly preferably attached to, the flexible pull member. Preferably, the holding part prevents substantial movement of the support part in one direction. In particular by the fact that the support part abuts, or bears, against the holding part, thus preventing further movement of the pull member in this direction. The holding part is in particular disposed on the supporting arm. Preferably, the pull member is accommodated, and in particular at least guided and/or even affixed, on the holding part at least in sections. The holding part is in particular disposed at least on the axle component and/or at least on the supporting component of the supporting arm. In particular does the holding part comprise, surround, guide, and/or reverse the flexible pull member. In this case, no separate guide member is required for guiding the flexible pull member. Preferably, the holding part shows a smooth contour layout absent any corners or edges, for guiding. Moreover, the holding part may be supported on, or disposed at, surrounding components or objects. Advantageously, the holding part enables transmitting the introduced operating force to the locking device. In a simple configuration, at least one holding part is affixed to the supporting arm and guides the pull member.

In at least one advantageous configuration, the contour of the holding part expands with increasing radial distance from a pivot axis. Advantageously, the expanding contour layout enables guiding and deflecting the flexible pull member. Moreover, the force transmission improves.

Preferably, at least one holding part is disposed at a radial distance from the pivot axis, corresponding to at least 20% of the maximum radial length of the supporting arm. Advantageously, at least one holding part is disposed at a radial distance corresponding to at least 30%, 50%, 70%, or a larger proportion of the maximum length of the supporting arm. Advantageously, at least one holding part is disposed radially outwardly of the attachment device.

Advantageously, an actuating member is disposed in the vicinity of the holding device. Advantageously, the actuation of the radiology holding device is thus particularly comfortable. Moreover, pivoting is advantageously feasible in a radial position showing a particularly long lever arm to the pivot axis, so that a user needs to apply only little force.

Particularly preferably, at least one actuating member, which can actuate the locking device, is disposed and/or attached radially outwardly of the attachment device. Advantageously, an actuating member is in particular disposed immediately adjacent to at least one holding device. A holding device may preferably be disposed in the vicinity of, or at, the radial end, i.e. given a large supporting arm radius. Advantageously, actuation may be done from the vicinity of a holding device. Optionally even by the patient, if safety is not significantly jeopardized. Furthermore, simple actuation may be performed by at least one assisting person.

Particularly advantageously, the support part surrounds or envelops the flexible pull member at least partially. Preferably, the support part serves to support and in particular to tension the flexible pull member. Preferably, a substantially defined position of the pull member and in particular that of the actuating member can thus be achieved. The support part advantageously fulfills the function of a "cable stopper", which biases, at least in sections, the flexible pull member that is in particular configured as a cable. Thus, a force can be transmitted substantially directly to the locking device.

The support part is in particular disposed on the pull member in a force-fit and/or form-fit. In at least one advantageous specific embodiment the support part is attached to, or accommodated on, a node section of the flexible pull member. Advantageously, the support part includes at least one receiving unit that can be at least partially closed. The receiving unit is in particular configured as a screw unit.

The pull member is preferably disposed on the lockable receiving unit. Advantageously, a permanent, stable connection between the support part and the flexible pull member can thus be achieved. The support part can in particular be locked on the pull member. To this end, the receiving unit and in particular the screw unit can preferably comprise at least one setscrew, by means of which the pull member can be at least partially locked on the support part. The position of the support part on the flexible pull member is preferably freely adjustable. Preferably, the connection is detachable, and all the components, exchangeable. This also allows to realize particularly high hygiene requirements.

Advantageously, the support part can be at least partially propped on the holding part. Preferably, the holding part can receive the support part. The support part is in particular matched to the contour of the holding part. Thus, the support part may show a tapered contour layout. The support part is in particular configured rotationally symmetrical, so that the support part self-centers on the holding part. Advantageously, the support part is propped on the holding part, at least during introduction of the operating force. Advantageously, the pull member thus directly transmits the operating force to the locking device. Using the support part particularly preferably ensures a safe and reproducible function of the force direction unit.

In particular with actuation of an actuating member disposed at a radial distance, a holding part, disposed at a greater radial distance than the actuated actuating member, locally locks movement of the transfer component, so that the operating force acts directly on the fixing member of the locking device.

In all the feasible advantageous configurations, the actuating mechanism can comprise at least two transfer components. Preferably, the transfer components are connected by at least one, in particular detachable, coupling unit. The coupling unit may extend the transfer components, or it may also enable changing between various transfer components. Thus, a force-fit connection can advantageously be established by way of the coupling unit. It is also possible to connect a transfer component configured as a rod member with a flexible pull member, by means of the coupling unit.

Preferably, the coupling unit may comprise at least one sleeve part. Advantageously, the coupling unit also comprises at least one screw unit. Advantageously, the transfer components are in particular configured as flexible pull members. Preferably, the sleeve part and the screw unit envelop the transfer components at least partially. The screw unit can in particular be configured as a setscrew, through which the transfer component passes at least partially. In particular, a flexible pull member is configured with at least one node section. Advantageously, the node section accommodates the pull member on the coupling unit, and preferably on the sleeve part and the screw unit. The configuration of the coupling unit enables connections of multiple transfer components for quick exchanges. Preferably, no tool is required for the coupling unit. Advantageously, two flexible node sections may be interconnected in a force-fit, solely by means of a connecting node section.

Advantageously, the transfer component is deflected and/or guided by at least one guide roller disposed outside of the axle component and/or at least one, disposed inside of the axle component. A deflection roller is preferably disposed on the axle component of the supporting arm. This allows particularly advantageous guiding of a flexible transfer component to at least one locking device. Movement of a transfer component can be deflected simply and directly to a desired direction. Movement of the deflection roller when actuating the actuating mechanism allows particularly low-friction guiding of the direction of movement of the transfer component. Particularly preferably, at least one deflection roller is disposed next to the axle component on which the transfer component is passed radially outwardly of the axle component. A deflection roller may also be disposed on the supporting arm, guiding the flexible pull member of the transfer component along the supporting arm.

Particularly preferably, the transfer component is deflected by at least one deflection sleeve. The deflection sleeve is in particular configured as a tube section, preferably showing a circular and/or elliptical and/or polygonal cross section. This allows to effectively adapt the acting direction of the transfer component, particularly preferably including inside of small radii. The deflection sleeve may also be configured as an at least partially open profile showing a U-shaped and/or V-shaped cross section. The guide can in particular be used for changing the orientation of the transfer component inside the hollow axle component, and when entering and exiting the axle component.

In a particularly preferable configuration variant, the transfer component is axially passed at least downwardly out of the axle component. Axially passing the transfer component out of the axle component advantageously allows deflecting the direction of a flexible pull member. Thus, the transfer component can exit the axle component centrally beneath the rotation axis of the supporting arm, so that the actuating mechanism can substantially be operated centrally.

A deflection sleeve advantageously enables deflecting the transfer component including in the case of small radii, and in places where no deflection roller can be disposed.

Advantageously, the radiology holding device comprises at least one limiting device for limiting a rotational angle. The rotational angle limiting device can particularly preferably be configured as a stopper that is disposed and/or attached, e.g. on or to the attachment device. The limiting device for limiting the rotational angle respectively the rotational angle limiting device serves to particularly preferably limit the rotational angle of the supporting arm to a total rotational angle, e.g. to a rotational angle of 270°, or 180°, or 90°. The concrete angle depends on the particular case, and the concrete conditions. Therefore, the rotational angle can be limited to a smaller total angle, which follows from the setup in the machine room and/or the pitch and the quantity of feasible locking positions. Configuring the radiology holding device without any limiting device is likewise feasible.

Particularly preferably, the rotational angle limiting device comprises a damper component which allows a soft, damped limit stop. The damper component is preferably configured as a rubber pad and/or a gas spring and/or a rubber pull. This allows a radiology holding device to be in particular disposed respectively incorporated in a radiology room so as to allow to adapt utilization to the requirements and the necessities of a radiology system, a patient or the operators, and to the geometric dimensions of the room. Preferably, the locking device can be provided with at least one stopper therefor. The limiting device can in particular be attached to the room wall. In this case, the limiting device is not incorporated in the locking device. In this way, a working area of the radiology holding device is defined.

In a particularly advantageous variant, the radiology holding device comprises a bumper unit, which encloses the radiology holding device in particular over large areas and/or in particular completely, protecting it (largely or nearly completely) against shocks and collisions with other devices in the radiology room, during pivoting.

Such a bumper unit is in particular suitable to protect the radiology holding device and/or other components of the radiology system from damage inflicted in operation. The damper unit particularly preferably has an (external) diameter of at least 100 or 150 mm, in particular 250 mm and/or 350 mm. However, smaller diameters are likewise conceivable, in dependence on the available mounting space and the conditions of the radiology room. The bumper unit is in particular configured on, and completely envelops, the supporting component of the supporting arm. The bumper unit can in particular, at least partially, also surround the axle component of the supporting arm. Advantageously, effective protection from damage is given.

Advantageously, the bumper unit comprises an elastic material, preferably rubber and/or plastic. The damper component can particularly preferably also comprise multiple materials. It is also possible for the bumper unit to particularly preferably comprise reinforcing members of hard plastic or metallic materials.

Particularly advantageously, the radiology holding device comprises at least one receiving rail having at least one hooking point or hooking spot, in which at least one holding device can be hooked. Advantageously, the receiving rail extends over at least a substantial part of the radial length of the supporting arm. The at least one receiving rail is configured along the supporting arm axis. A receiving rail may be configured flexurally rigid so that it extends at least over 25%, 50%, 75% or even up to 100% of the radial length of the supporting arm. However, the length of a receiving rail may be distinctly shorter than the length of the supporting arm. In particular, multiple receiving rails may be disposed along the supporting component. This makes the configuration particularly torsionally rigid, offering a high moment of resistance in the case of loads at normal and/or transverse forces and/or bending moments.

The holding device comprises in particular at least one hooking member for hooking into the receiving rail. It is in particular configured as a, or comprises at least one, hook member and in particular a snap hook (karabiner), or an open hook. In particular, multiple hooking points or hooking spots are disposed and/or configured along the receiving rail. The receiving rail is particularly preferably connected with the supporting arm at both ends. The length of a receiving rail may be distinctly shorter than the length of the supporting arm. This makes the configuration particularly torsionally rigid, offering a high moment of resistance in the case of loads at normal and/or transverse forces and/or bending moments.

In particular, at least two receiving rails are disposed over the entire length of the supporting arm, so that each point in the primarily circular operating range is accessible by the holding device.

The holding device comprises in particular at least one hooking member for hooking into the receiving rail. It is in particular configured as a, or in particular comprises at least one, hook member and in particular a snap hook (karabiner), or an open hook. In the case of an open hook member, the legs of the hook are preferably dimensioned so as to enable very large retaining angles of 45° and more.

Preferably, the holding device allows a retaining angle of at least 45°. The retaining angle is advantageously measured relative to the vertical. The retaining angle is preferably open in the direction of a gravity acceleration vector. Preferably, retaining angles of up to 60° and more are possible. Thus, a stable support is particularly advantageously achieved in nearly any conceivable position. Removing a holding device from the receiving rails by means of an open hook is preferably only possible in the case of angles relative to the vertical exceeding in particular 30° and preferably 45° and particularly preferably 60°. Sufficiently pivoting the holding device respectively the open hook relative to the vertical, and pushing the open hook obliquely upwardly, the open hook can be removed, and the holding device can be hooked, by means of the open hook, in another position on the receiving rail or in another receiving rail.

To advantageously support the holding device, at least one additional support hook can be disposed e.g. at the extreme end of the supporting arm, or in various longitudinal spots for supporting the holding device (when not in use). Due to hooking the holding device in the support hook, the holding device is no obstacle during pivoting motions of the supporting arm. This enables particularly advantageously a simple, safe, and readily variable safeguard of the holding device.

A hooking point or a hooking spot can provide a lock-in position of the holding device. The function of the receiving rail is not limited to the hooking device. It can in particular also be used for holding infusions respectively infusion bags and/or infusion holders. Utilization for other functions is likewise conceivable. Separate infusion holders are conceivable as well.

The receiving rail is particularly preferably made of a stainless, metallic material, in particular "VA steel" or another stainless steel alloy. In particular is the material surface configured so as to dispense with paint coating and to generate hardly any abrasion, or none at all, due to mechanical wear.

Alternately, the receiving rail can be configured transverse or obliquely to the supporting arm, and in particular to the supporting component. It is also possible to dispose two or more receiving rails on at least one supporting arm. The receiving rail is advantageously configured such that a holding device can move between multiple, different hooking points or hooking spots, without requiring the entire retaining device to be unhooked out of the receiving rail. Particularly preferably, two receiving rails are configured over the entire radial length of the supporting arm, each preferably only covering a partial length. Then, unhooking is only required in the case that the holding device must be transferred for example from a receiving rail to another receiving rail. Three or more receiving rails are likewise conceivable.

The hooking points are preferably formed by shaped members, into which an annular member of the holding device engages, advantageously in the case of a tensile load. The hooking points or hooking spots may be formed by local "valleys" in the receiving rail, limited by local "hills" in-between. Thus, the position of the holding device can be changed along the supporting arm, without requiring release of the form-fit connection between the receiving rail and the holding device. This allows to simply and quickly adapt and modify the position of the holding device between a plurality of positions. To this end, the holding device is simply pushed further into the next hooking point respectively lifted over the next "hill". The holding device does not require complicated demounting therefor, so that it cannot drop down while the hooking position is being changed. The injury potential for users is minimized.

Particularly advantageously, the holding device comprises a belt unit. The belt unit is particularly advantageously disposed between the hooking member and the grip member. The belt unit primarily serves to facilitate sitting up and shifting for a patient. To this end, the length of an enveloped belt member can be modified, optionally motor-assisted, to the requirements and conditions of a user.

Particularly preferably, the belt unit, when ready to use, is supported for rotation about an axis oriented transverse to the horizontal. Particularly preferably, the belt unit is supported for easy gliding, so that, as the holding device or a holding grip of the holding device rotates, the belt unit rotates around its point of support, so as to not twist the belt per se, or only minimally. Preferably, the belt unit rotates around its point of support considerably more than the belt is twisted, as the holding device pivots.

The belt is preferably formed by a wide fabric band. Advantageously, the belt does not twist at all, or only insignificantly, when used as intended. Adapting the length primarily serves to advantageously adapt the length of the holding device to the user and his/her position, so as to allow an advantageous support and/or shifting in various positions.

A (motor-assisted) drive of the belt unit can particularly preferably be provided by a winding spring, or optionally also by electric motor configured in particular as a positioning motor. The controlling can particularly advantageously be provided by a control unit which can be operated and/or controlled directly at the holding device or by remote control. An alternative configuration of the motor-assisted drive as a pneumatic and/or hydraulic motor is conceivable as well.

In all the configurations it is possible that patients actively assist in shifting or transferring themselves. Moreover, the belt unit particularly advantageously enables patients to lift themselves with the aid of the supporting unit or the holding grip, assisting in their being shifted. Thus, patients can be shifted by supporting units configured as a stretcher or chair or transfer cloth. Other types and embodiments of supporting units are likewise possible.

Advantageously, the support required from the nursing or radiology staff in shifting is also minimized. In an ideal case, a nurse is substantially not required to assist in shifting. In this way, the risk of contagion by bacteria, viruses and germs is minimized. The potential of sexual harassment during shifting is clearly minimized. Loss of working hours due to mental stress or by transmitted germs is clearly minimized. This primarily improves the operability and also the profitability of radiology systems.

Advantageously, the radiology holding device is at least partially manufactured of materials which cannot be magnetized at all or only with difficulties and/or only to a slight degree. Operating radiology apparatus may generate high intensity magnetic fields. Metallic materials showing a specific molecular structure might thus be magnetized, which might cause interaction with the radiology apparatus. Therefore, all the components and parts of the radiology holding device are preferably manufactured of only slightly and in particular not at all magnetizable materials, such as plastic and/or aluminum and/or stainless steel. Advantageously, however, at least large parts of the radiology holding device are at least partially manufactured of materials that cannot be magnetized at all or only with difficulties. This allows to exclude and/or at least minimize, magnetic interactions (and thus artefacts in the images) between the radiology holding device and the radiology apparatus. This primarily serves for a safe and reliable operation of the radiology apparatus and high quality of the images made thereby.

Particularly preferably, a radiology system according to the invention comprises at least one radiology apparatus and at least one radiology holding device.

In at least one advantageous specific embodiment, at least one transfer component is passed, at least in sections, through a hollow section of the supporting component. Advantageously, a force direction unit may also be at least partially disposed inside of the supporting component. Thus, the pull member can in particular be protected hygienically from contamination.

Advantageously, the radiology system comprises at least one accommodation for patients for examination by means of the radiology apparatus, which is at least partially disposed in the operating range of the radiology holding device. Preferably, the patient accommodation is disposed centrally in the operating range of the radiology holding device, so that the operating range of the radiology holding device can be efficiently used.

Figure 2:
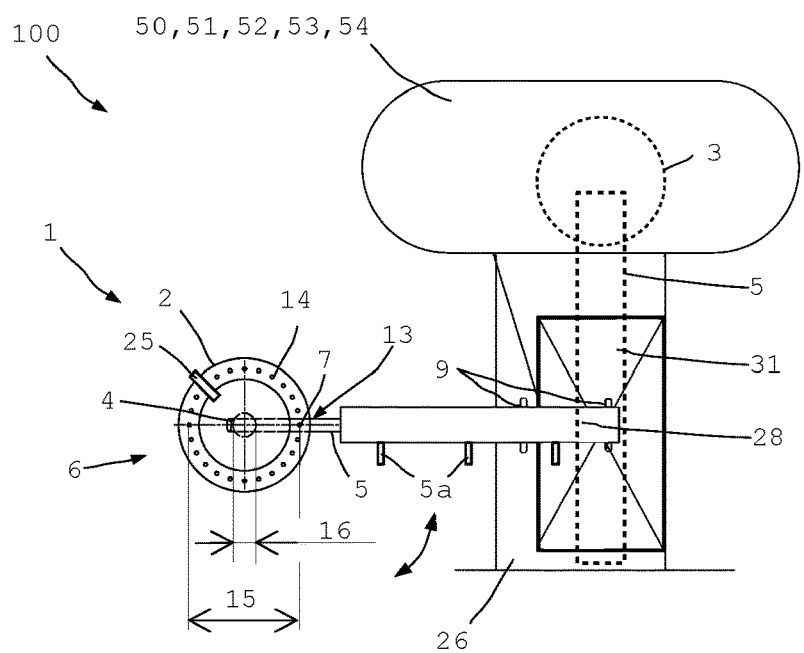
Figure 3:
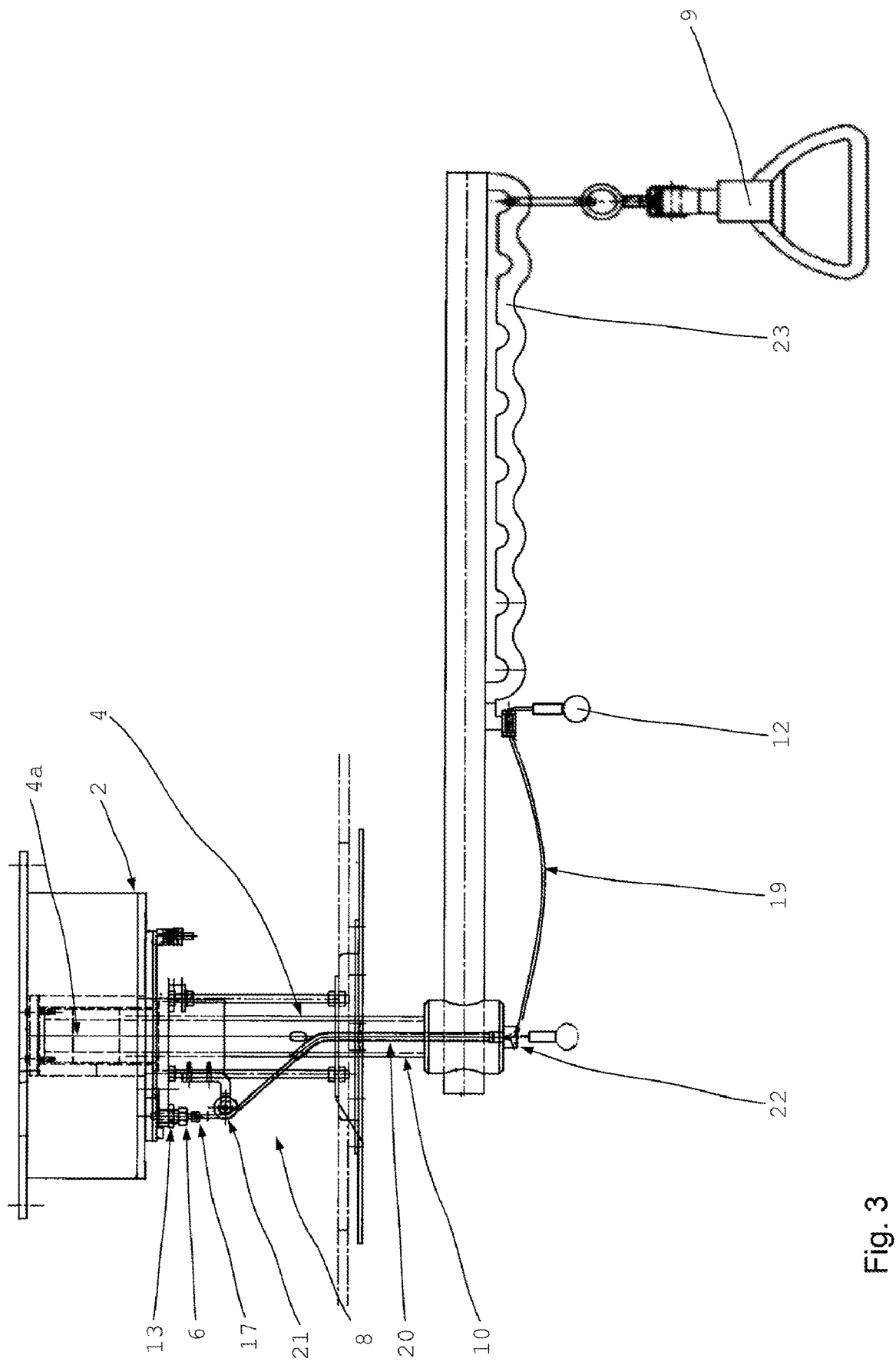
Figure 4:
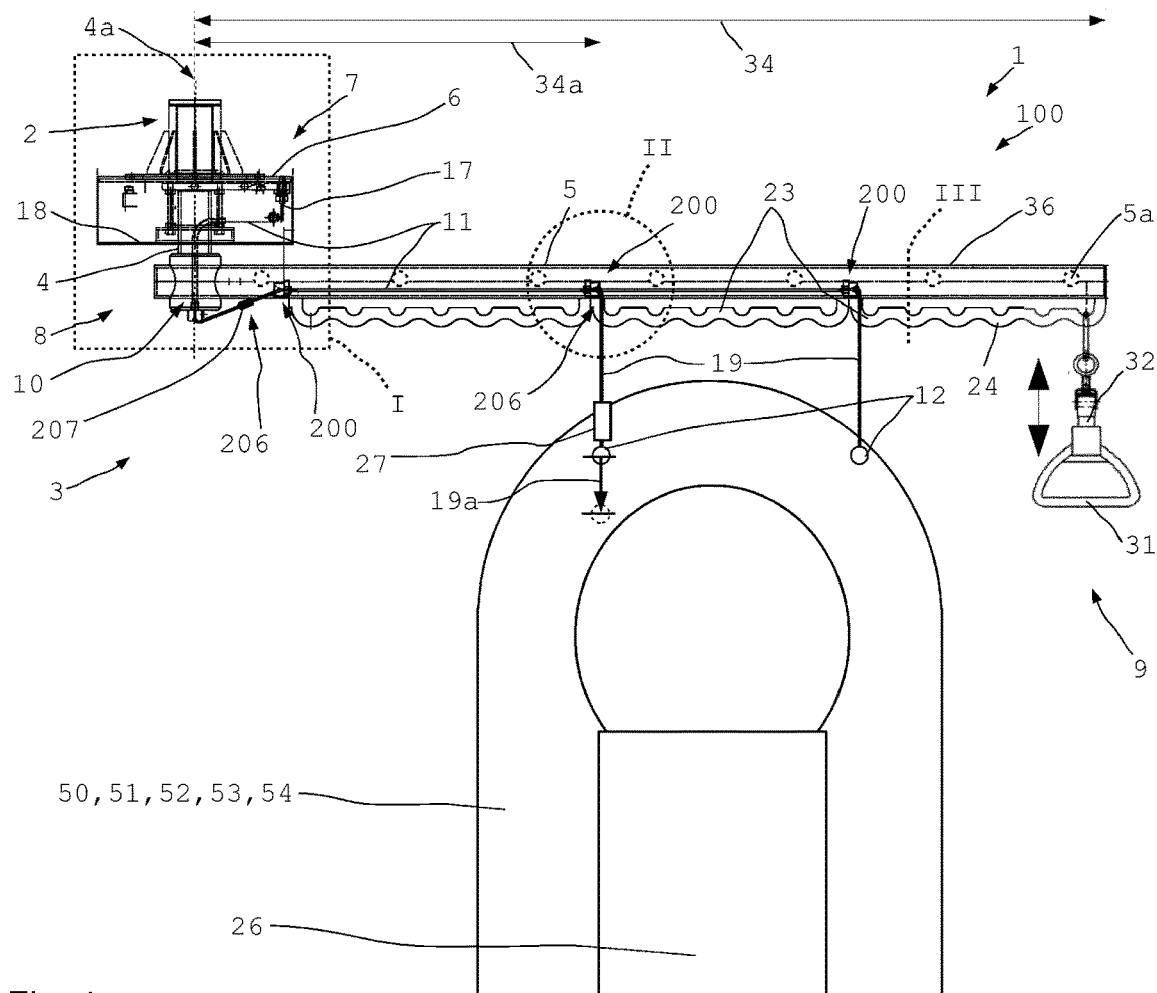
Figure 5:
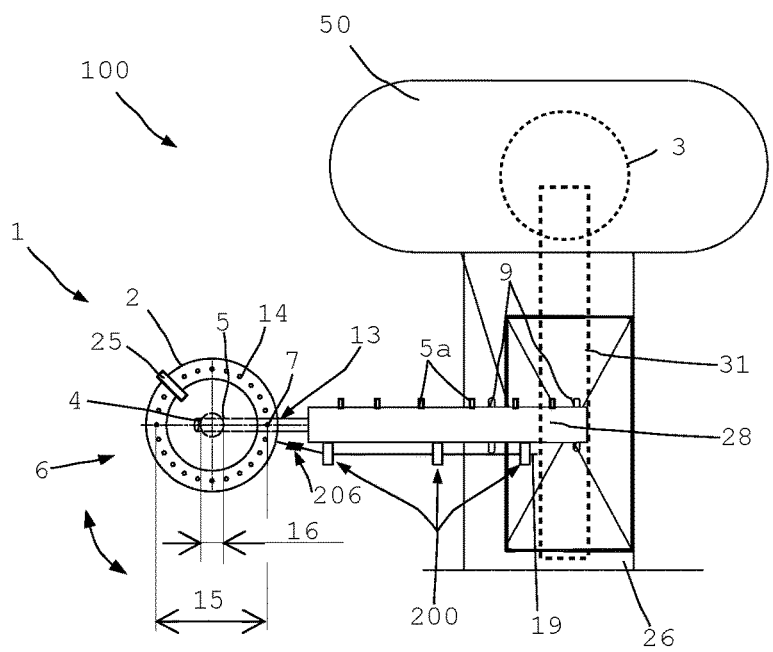
Figure 6:
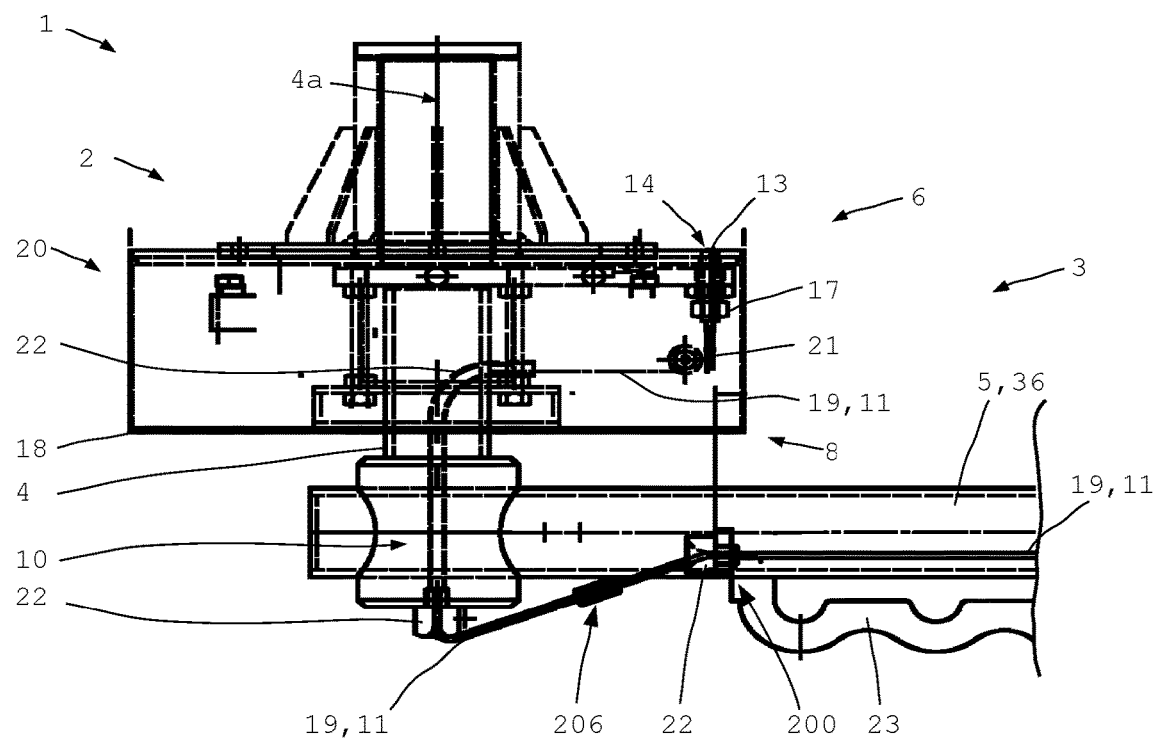
Figure 7:
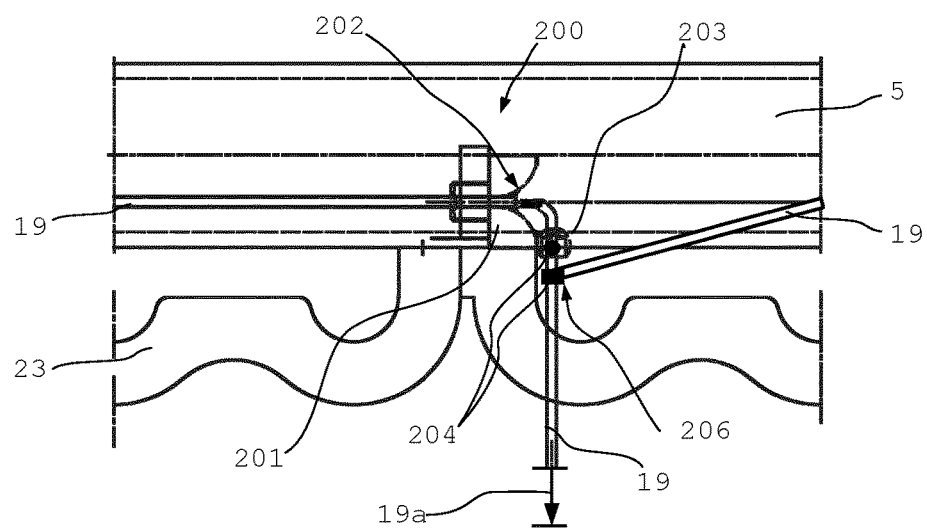
Figure 8:
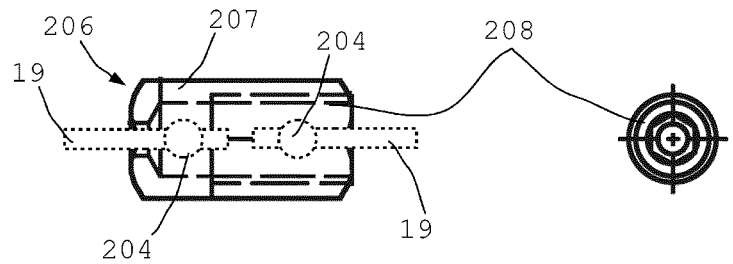
Figure 9:
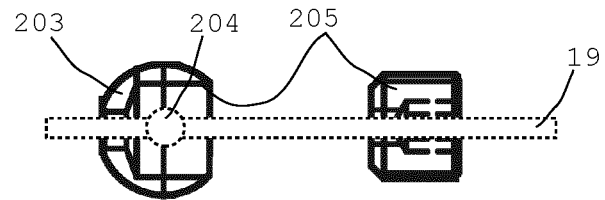
Figure 10:
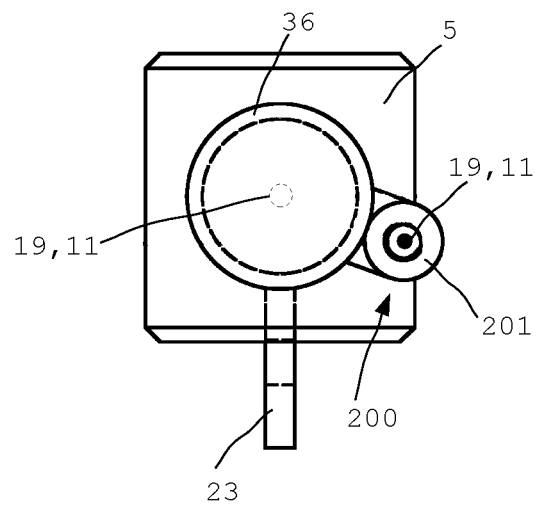
Figure 11:
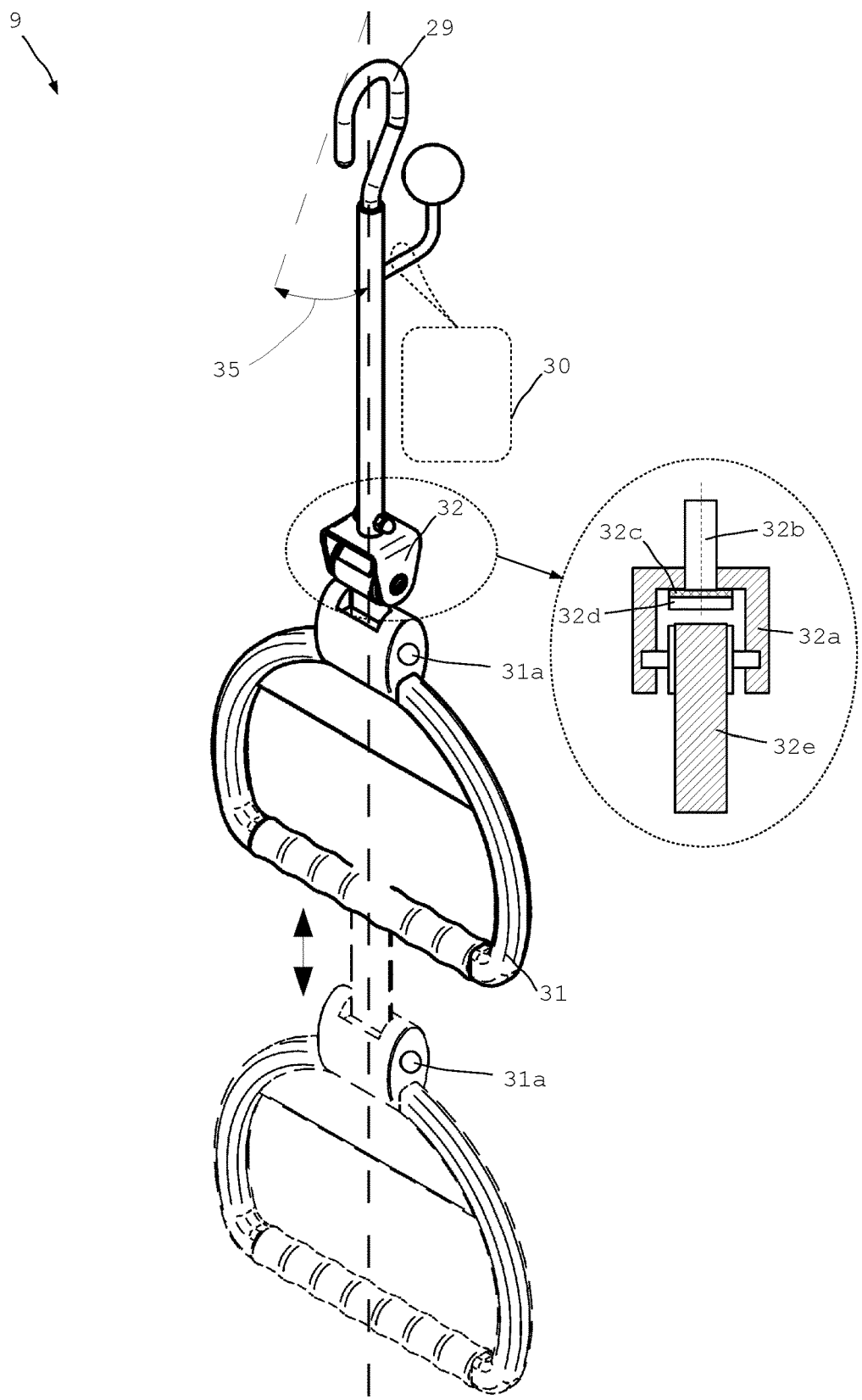

Further advantages and features of the present invention can be taken from the exemplary embodiments which will be discussed below with reference to the enclosed figures. The figures show in:

FIG. 1 a front view of the radiology system with a sectional view of a first exemplary embodiment of a radiology holding device according to the invention, and the front view of a radiology apparatus;

FIG. 2 a top view of a radiology system with a radiology holding device according to the first exemplary embodiment, and a radiology apparatus disposed in the operating range;

FIG. 3 an enlarged sectional view of a radiology holding device according to the first exemplary embodiment;

FIG. 4 a front view of the radiology system with a sectional view of a second exemplary embodiment of a radiology holding device according to the invention, and the front view of a radiology apparatus;

FIG. 5 a top view of a radiology system of a radiology holding device according to the invention according to the second exemplary embodiment, and a radiology apparatus disposed in the operating range;

FIG. 6 an enlarged partial view of the axle component of the exemplary embodiment of a radiology holding device according to the invention according to the second exemplary embodiment;

FIG. 7 an enlarged sectional view of a force direction unit of a radiology holding device according to the invention according to the second exemplary embodiment;

FIG. 8 a detail view of a coupling unit of a radiology holding device according to the invention according to the second exemplary embodiment;

FIG. 9 a detail view of a support part of a radiology holding device according to the invention according to the second exemplary embodiment;

FIG. 10 an enlarged sectional view of a supporting component of a radiology holding device according to the invention according to the second exemplary embodiment;

FIG. 11 a perspective view of a holding device of a radiology holding device according to the invention according to the second exemplary embodiment.

FIG. 1 shows a view of a first exemplary embodiment of the radiology system 100 according to the invention. The radiology holding device 1 is shown in a sectional view, while the radiology apparatus 50, such as an X-ray apparatus 51, MRT apparatus 52, CT apparatus, or a radiotherapy apparatus 54, is shown in a front view. The radiology holding device 1 comprises an attachment device 2, which pivotally accommodates and bears the supporting arm 3. The supporting arm 3 comprises an axle component 4, which is pivotally fixed to the attachment device 2, and a supporting component 5.

The attachment device 2 is presently configured as an attachment console and is fixedly mounted to the ceiling of a radiology room (not shown). The shield 18 is centrally disposed on the axle component 4, covering the opening, which is formed by means of the passage of the supporting arm 3 through the magnetically shielding intermediate ceiling. In the case that the radiology holding device 1 does not pass through an intermediate ceiling, the shield 18 is preferably configured such that it completely encloses the attachment device 2.

The radiology holding device 1 is disposed in the vicinity of a radiology apparatus 50, such as an X-ray apparatus 51, MRT apparatus 52, CT apparatus 53 or radiotherapy apparatus 54. The supporting arm 3 can be pivoted over the patient treatment table 26, so that the holding device 9 is readily accessible for a patient.

Along the supporting component 5, two receiving rails 23 are configured with multiple hooking points 24 over the entire length of the supporting component 5. In a hooking point 24 of the receiving rail 23, a holding device 9 is hooked, which a patient can hold on to for support during shifting and positioning. An infusion bag 30 may also be hooked into a hooking point 24 of the receiving rail 23. A hooking point 24 of the receiving rail 23 is configured as a "valley" between two "hills" in the contour of the receiving rail 23. A tensile load applied on the holding device 9, as in normal use, fixes the position of the holding device 9 in the hooking point 24 in a form-fit due to the "valley" geometry. The holding device 9 comprises a motor-driven or preferably mechanically, spring-driven belt unit 32, by means of which the length of the holding device 9 is variably adjustable. A support hook 29a for the holding device 9 is disposed at the end of the supporting component 5. The holding device 9 can be placed across the support hook 29a, so that it does not interfere when pivoting the supporting arm 3.

Two receiving rails 23 are configured on the supporting component 5 immediately radially adjacent to the grip knob as an actuating member 12. Each of the receiving rails 23 comprises multiple hooking points 24. The hooking points 24 are configured as "valleys" in the contour of the receiving rail 23. In the hooking points 24, a holding device 9 formed by a grip and two hook members, is hooked into the outermost hooking point 24. The "valleys" of the receiving rail 23 serving as hooking points 24 are separated from one another by "hills" in the contour. A tensile load as applied in normal use fixes the position of the ring loop of the holding device 9 in the hooking point 24. The holding device 9 can readily be pushed into another hooking point 24 over a "hill", without having to remove a leg of the hook. This provides a safe construction showing load capacity.

The actuation of the actuating mechanism 8 allows to transfer the supporting arm 3 locked in the locking position 7 by the locking device 6, to a rotary position, counter to the force of the biasing device 17. In the rotary position, the supporting arm 3 is pivotable around the rotation axis 4a of the axle component 4.

The transfer component 11 is configured as a flexible pull member 19 and connected with the locking device 6. The transfer component 11 is configured as a pull rope, which passes through the hollow section of the axle component 10 axially downwardly, outwardly out of the axle component 4, and guided and disposed radially along the supporting component 5. One of the actuating members 12 can actuate the actuating mechanism 8. A protective sleeve 27 is disposed on the transfer component 11 as a protection from contamination. They are formed by the cable loop, i.e. the transfer component 11, and a knob or the like.

The knob as the actuating member 12 is disposed immediately adjacent to the receiving rail 23. This allows a comfortable and simple actuation.

FIG. 2 shows a plan view of the radiology system 100, comprising a radiology apparatus 50 and a supporting arm 3 according to the first exemplary embodiment. The attachment device 2, see FIG. 1, is not illustrated, so that the locking device 6 is visible in a top view. The supporting arm 3 is pivotable around the rotation axis 4a of the axle component 4 configured as a tube section.

The locking device 6 comprises a fixing member 13 which is fixed to the supporting arm 3 and is biased in the locking position 7 by the biasing device 17. The fixing member 13 is configured as a bolt which engages in a depression 14 of a hole circle 15 of the locking device 6. The diameter of the depressions 15 is noticeably larger than the diameter of the axle component 16. Thus, the locking device 6 can be disposed in a simple structure, radially outwardly of the axle component 4, enabling safe fixing.

A limiting device 25 for the rotational angle is provided. The limiting device 25 for the rotational angle is configured as a mechanical stopper which limits the rotational angle of the supporting arm 3. The stopper is fixed in a depression 14.

A shock device 28 protects the supporting arm 3 from shocks and against damage. Simultaneously, the shock device 28 constitutes effective protection against damaging other objects.

On the holding device 9, a patient supporting unit 31 is fastened, which the belt unit 32 can displace upwardly and downwardly.

The housing of the belt unit 32 may be provided with an operating knob 31a (see FIG. 11), which serves for the actuation of a reel-up unit driven e.g. by a winding spring (not visible since disposed in the interior). When operating the knob 31a, the belt can be automatically retracted and reeled up (not subjected to a load) or the belt can be pulled out, against the force of the winding spring. Preferably, a belt length of at least 200 or 300 mm is provided. In advantageous configurations, the extendible belt length may be 500 mm or 750 mm or more. In high-ceilinged rooms this offers the advantage that, when not in use, the holding grip of the holding device 9 can be raised high enough so as to not be in the way when not in use, and hitting one's head is prevented. Alternately, it is also possible to hang the holding grip not in use in one of the hooks 5a.

FIG. 2 shows in a broken line a variant where the supporting arm 3 is accommodated or configured on the radiology apparatus 50. The advantage thereof is that the attachment device 2 is accommodated directly on the radiology apparatus 50, so as to enable a compact structure on the whole.

The hooks 5a shown in the FIGS. 1 and 2 allow hanging objects. For example, infusion bags may be attached thereto, or patient documentation appended thereon. The hooks 5a may be attached on, e.g. welded to, the sides of the supporting component 5. It is also possible to accommodate and attach the hooks 5a to the supporting component, stationary or displaceably, by means of tube clamps or specific attachment systems.

FIG. 3 shows an enlarged sectional view of an axle component 4 and part of the supporting component 5 of the radiology holding device 1 according to the first exemplary embodiment. The attachment device 2 is configured as an attachment console. The attachment device 2 can be fastened by screwed connection to the ceiling of the radiology room—not shown. The pivotable supporting arm 3 is accommodated and supported on the attachment device 2. To this end, the pivotable axle component 4 is directly connected with, and disposed on, the attachment device 2. The supporting component 5 extends transverse to the axle component 4. The supporting arm 3 is pivotable around the central rotation axis 4a of the axle component 4.

The axle component 4 is passed through an intermediate ceiling. The intermediate ceiling is merely outlined by the broken lines, not illustrated completely.

A shield 18 is disposed centrally on the axle component 4. Thus, the aperture in the intermediate ceiling is closed and covered. A magnetic shielding located in or on the intermediate ceiling can thus be effectively covered and closed. The shield 18 comprises a magnetic shielding, so that the remaining aperture of the magnetic shielding is as small as possible.

The locking device 6 locks the supporting arm 3 by a fixing member 13 in the locking position 7 shown. As a rule, it is biased in the locking position 7 by a biasing device 17, presently configured as a coil spring. The supporting arm 3 is non-rotatably fixed in the locking position 7. Thus, safety of using the radiology holding device 1 can be ensured.

The actuating mechanism 8 can operate the locking device 6. The fixing member 13 is connected with the transfer component 11. The transfer component 11 is configured as a flexible pull member 19, specifically as a pull rope.

The transfer component 11 is radially guided to the axle component 4 by means of a guide roller 21. The transfer component 11 is radially guided by a guide unit 20, through the wall of the axle component 4, from the outside to the inside (and vice versa). Inside the axle component 4, the transfer component 11 is guided by the guide unit 20 along the axis of the axle component 4. The guide unit 20 is presently configured as a tube. The tube is bent for deflecting the transfer component 11.

At the lower end of the axle component 4, the transfer component 11 is axially passed out of the axle component 4. At the lower end of the axle component 4, a deflection sleeve 22 is attached. The deflection sleeve 22 is configured as a conical tube section or sleeve. The deflection sleeve 22 is preferably manufactured of a plastic showing a particularly slidable and smooth surface, thus offering low frictional resistance. This allows to deflect the transfer component 11 in a small radius in the direction of the supporting component 5 of the supporting arm 3. The supporting component 5 may be a separate part, or it may be configured integrally with the supporting arm 3.

The transfer component 11 is passed through the intermediate ceiling inside of the axle component 4. Thus, it does not require a separate guide through the intermediate ceiling outside of the axle component 4. An opening in the intermediate ceiling is therefore clearly smaller than with a pull rope simply hanging down straight and in parallel to the axis of the axle component 4. The required opening of the magnetic shielding in an intermediate ceiling is clearly smaller and easier to close than in the designs known in the prior art.

At the supporting component 5, the transfer component 11 is deflected along the axis of the supporting component 5, and guided further along the axis of the supporting component 5. The transfer component 11 forms a cable loop which is guided on another guide member. A knob is attached on the radially outwardly side of the guide member. The knob and the cable loop both serve as actuating members 12, which can actuate the actuating mechanism 8.

Two receiving rails 23 are configured on the supporting component 5 immediately radially adjacent to the knob as the actuating member 12. Each of the receiving rails 23 comprises multiple hooking points 24. The hooking points 24 are configured as "valleys" in the contour of the receiving rail 23. In the hooking points 24, a holding device 9 formed by a grip and two ring loops, is hooked into the outermost hooking point 24. The "valleys" of the receiving rail 23 serving as hooking points 24 are separated from one another by "hills" in the contour. A tensile load as applied in normal use fixes the position of the ring loop of the holding device 9 in the hooking point 24. The holding device 9 can readily be pushed into another hooking point 24 over a "hill", without having to open a ring loop. This provides a safe construction showing load capacity.

FIG. 4 shows a view of the radiology system 100 according to the invention according to the second exemplary embodiment. Here, the transfer component 11 configured as a flexible pull member 19, is guided horizontally along the supporting arm 3. A total of three force direction units 200 are provided. The force direction units 200 ensure actuation at a consistent actuation travel 19a.

The attachment device 2 is presently configured as an attachment console and is fixedly mounted to the ceiling of a radiology room (not shown). The shield 18 is centrally disposed on the axle component 4, covering the opening, which is formed by means of the passage of the supporting arm 3 through the magnetically shielding intermediate ceiling. In the case that the radiology holding device 1 does not pass through an intermediate ceiling, the shield 18 is preferably configured such that it completely encloses the attachment device 2.

In the hooking points 24, a holding device 9 is provided, formed by a grip showing at least one hook member 35. The holding device 9 is illustrated and described in FIG. 11 in detail.

The actuating mechanism 8 comprises a total of three transfer components 11, all of which are configured as flexible pull members 19, and more precisely, as pull ropes. Here, the first transfer component 11 is connected with the locking device 6. Here, the first transfer component 11 is configured as a pull rope, which is guided outwardly through the hollow section of the axle component 10, axially downwardly, out of the axle component 4, and is radially guided toward, and disposed at, the supporting component 5. Here, the first transfer component 11 shows another transfer component 11 connected therewith by means of a coupling unit 206, and passed radially further outwardly along the supporting component 5. The second pull member 19 extends horizontally along the supporting component 5, guided up to the force direction unit 200. The flexible pull member 19 is guided on the force direction unit 200 and deflected downwardly. Here, two force direction units 200 are disposed, so as to transmit an operating force introduced into the flexible pull member 19, directly to actuating the locking device 6. A third transfer component 11 is connected to the central force direction unit 200 by means of another coupling unit 206. A force direction unit 200 is likewise provided for the third transfer component 11.

Here, the force direction units 200 comprise a holding part 201 each, which is fixedly connected with the supporting component 5 of the supporting arm 3. In the vicinity of the retaining member 201, a support part 203 is disposed on the flexible pull member 19 and connected with the flexible pull member 19 in a force-fit. When a user pulls the actuating member 12, the support part is moved on the holding part 201 of a force direction unit 200, whose radial distance 34a to the actuating member 12 is longer. Thus, the force transfer inside of the transfer component 11 is transferred controlled to the locking device 6. In actuation, the flexible pull member 19 cannot be pulled reversely out of the leading holding part 201. This preferably provides a short and defined actuation travel 19a.

A grip knob of the actuating member 12 is disposed immediately adjacent to the receiving rail 23. This allows a comfortable and simple actuation. A holding part 201 is disposed radially outwardly of the attachment device 2, approximately at half the length 34 of the supporting component 5 of the supporting arm 3. The second holding part 201 is disposed at a radial distance 34 corresponding to approximately 75% of the length 34 of the supporting arm 3 of the radiology holding device 1. This allows comfortable actuation by users in the vicinity of the holding device 9. Moreover, the force for pivoting can thus be introduced, in the case of a large radial distance 34a from the rotation axis 4a, i.e. involving a long lever arm.

When actuating the locking device 6 by the first actuating member 12 showing the shorter radial distance 34a to the rotation axis 4a, it is advantageously ensured by way of the force direction unit 200 disposed at a larger radial distance 34a, that the pull member is not pulled out of the guide of the holding part 201. The support part 203 prohibits movement of the flexible pull member 19. Thus, the operating force is transferred directly to the locking device 6 for actuation. The flexible pull members 19 cannot unintentionally or undefinably sag due to the force direction units 200. The actuation travel 19a is defined and definable by the force direction unit 200. Substantially, the actuation travel 19a corresponds to the stroke length required for actuation of a fixing member 13, which is pulled out of a depression 4 of the locking device 6 for transferring the supporting arm 3 to the rotary position.

FIG. 5 shows a plan view of the radiology system 100, comprising a radiology apparatus 50 and a supporting arm 3 according to the second exemplary embodiment. The attachment device 2, see FIG. 4, is not illustrated, so that the locking device 6 is visible in a top view.

The three force direction units 200 are laterally disposed along the supporting component 5 of the supporting arm 3. The holding parts 201 of the force direction units 200 comprise and guide the flexible pull members 19. The support parts 203 are fixedly connected with the flexible pull members 19. When actuated, the support parts 203 move together with the flexible pull member 19. The actuating members 12 are not illustrated here.

FIG. 6 shows an enlarged sectional view of an axle component 4 and part of the supporting component 5 of the radiology holding device 1 according to the second exemplary embodiment, cf. region I in FIG. 4. The attachment device 2 is configured as an attachment console. The attachment device 2 can be fastened by screwed connection to the ceiling of the radiology room—not shown. The pivotable supporting arm 3 is accommodated and supported on the attachment device 2. To this end, the pivotable axle component 4 is directly connected with, and disposed on, the attachment device 2. The supporting component 5 extends transverse to the axle component 4. The supporting arm 3 is pivotable around the central rotation axis 4a of the axle component 4.

The locking device 6 locks the supporting arm 3 by a fixing member 13 in the locking position 7 shown. The fixing member 13 is biased in the locking position 7 by a biasing device 17, presently configured as a coil spring. The supporting arm 3 is non-rotatably fixed in the locking position 7. Thus, safety in using the radiology holding device 1 can be ensured.

The actuating mechanism 8 can operate the locking device 6. The fixing member 13 is connected with the transfer component 11. The transfer component 11 is configured as a flexible pull member 19, more precisely as a pull rope.

The transfer component 11 is radially guided to the axle component 4 by means of a guide roller 21. The transfer component 11 is deflected by the guide roller 21 and guided by a guide unit 20 inside of the axle component 4 along the axis of the axle component 4 through the guide unit. The guide unit 20 presently comprises a tube. The tube is bent for deflecting the transfer component 11.

At the lower end of the axle component 4, the transfer component 11 is axially passed out of the axle component 4. At the lower end of the axle component 4, a deflection sleeve 22 is attached. The deflection sleeve 22 is configured as a conical tube section or sleeve. The deflection sleeve 22 is preferably manufactured of a plastic showing a particularly slidable and smooth surface, thus offering low frictional resistance. This allows to deflect the transfer component 11 in a small radius in the direction of the supporting component 5 of the supporting arm 3. The supporting component 5 may be a separate part, or it may be configured integrally with the supporting arm 3.

At the supporting component 5, the transfer component 11 is deflected in the horizontal direction along the axis of the supporting component 5, and guided further along the axis of the supporting component 5. A second transfer component 11 is connected with the first transfer component by the coupling unit 206. The force direction unit 200 ensures an optimal transfer of the introduced operating force. An undefined and above all, unintended sagging of the flexible pull member 19 is prevented.

FIG. 7 shows an enlarged illustration of a region of the supporting arm 3 with a force direction unit 200 in the actuated state of the radiology holding device 1 according to the second exemplary embodiment, see region II in FIG. 4. The holding part 201 of the force direction unit 200 is firmly connected with the supporting component 5 of the supporting arm, for example by screw-connection or welding, enclosing the flexible pull member 19 sleeve-like. The support part is accommodated on the flexible pull member 19 by force-fit. The spherical support part 203 is firmly connected with the pull rope. The position of the support part 203 on the flexible pull member 19 is adjustable variably.

A contour layout 202 of the holding part 201 expands with increasing distance 34a from the rotation axis 4a. This allows to advantageously deflect the flexible pull member 19 on the holding part 201 so as to enable actuation of the locking device 6. The contour layout 202 of the holding part is funnel-shaped. The pull member 19 is deflected downwardly, where the actuating member 12, not shown, is disposed.

The support part 203 is configured spherical and hollow inside. The pull member 19 is passed through the support part 203. The pull member 19 is configured with a node section 204 which is accommodated inwardly on the support part 203. Moreover, the support part 203 comprises a screw unit 205, which is configured as a setscrew. The pull member 19 passes through the setscrew. The setscrew is screwed into the support part 203. Thus, the support part is connected with the pull member 19 in a force-fit.

The spherical support part 203 can be accommodated on the holding part 201 of the force direction unit 200. The support part 203 is centered on the rotationally symmetrical, sleeve-like holding part 201. The pull member 19 shows another pull member 19 connected in a force-fit by means of a coupling unit 206. This coupling unit is formed by a node section 204. The further pull member 19 is disposed on the first pull member 19 in a force-fit by way of the node section 204, and firmly connected therewith. This coupling unit is formed by a node section 204. The further pull member 19 is disposed on the first pull member 19 in a force-fit by way of a node section 204.

FIG. 8 shows an embodiment of the coupling unit 206 in a sectional view according to the second exemplary embodiment. The coupling unit 206 comprises a sleeve part 207. Two transfer components 11 are disposed inside of the sleeve part. One node section 204 each is configured on the transfer components 11, presently configured as flexible pull members 19. The sleeve part 207 of the coupling unit 206 is closed by a screw unit 208. The screw unit 208 is presently configured as a setscrew, through which one of the pull members 19 passes. In a closed state, the two pull members 19 are connected in a force-fit. The illustration of the pull member 19 by broken lines is intended to illustrate a conceivable arrangement of the flexible pull member 19 on the coupling unit 206. Moreover, further arrangements and connections of the pull members 19 are possible and conceivable. This also applies to the following Figures.

FIG. 9 shows a sectional view of a support part 203 of the force direction unit 200 according to the second exemplary embodiment. The support part 203 is configured spherical. The support part 203 is configured as a spherical sleeve part 207. The pull member 19 is accommodated on the support part 203 by means of a node section 204 configured thereat. The support part is closed by the receiving unit 205, presently configured as a screw unit 205, so that a force-fit connection is provided. The support part 203 can be disposed in almost any desired position of the flexible pull member 19.

FIG. 10 shows a sectional view of the supporting component 5 of the supporting arm 3 of the radiology holding device 1, transverse to the axis of the supporting component 5 according to the second exemplary embodiment, see region III in FIG. 4. The holding part 201 is laterally disposed on the supporting component 5. The holding part 201 encloses and guides the flexible pull member 19. The support part 203 is not illustrated. It is also possible for the pull member 19 to be passed through a hollow section of a tube element 36 of the supporting component 5. Thus, the transfer component 11 is advantageously protected from contamination. Users cannot be entangled in the pull member 19. In this case, the risk of injury is particularly minimized.

FIG. 11 shows a perspective view of a holding device 9 for a radiology holding device 1 according to the invention according to the second exemplary embodiment. The holding device 9 comprises a hook member 29, with which the holding device can be received in a hooking point 24 of the receiving rail 23. Another support hook 29a is disposed on the holding device 9 to accommodate additional objects, such as an infusion bag 30. The holding grip 31 can advantageously be flipped up and hooked into the support hook 29a. This minimizes the risk of injury and shocks. The long legs of the hook allows large retaining angles 35 of up to 60° and more, without risking that the leg of the hook slips out of the receiving rail 23.

In FIG. 11, one can identify the knob 31a, which is configured on the belt unit 32 and presently, on the holding grip of the holding device 9, to pull out the belt 32e by way of a winding spring, not visible and disposed in the interior, or against the tensioning force of the winding spring. The holding grip is accommodated on the rod 32b for rotation with the belt unit 32. The belt unit 32 is accommodated for pivoting via the sliding member 32c. The sliding member 32c serves as a bearing unit and is accommodated between the upper bracket of the holder 32a and the enlarged head 32d of the rod 32b, to as to enable easy-glide pivoting of the belt unit in the direction toward a patient. Although the belt 32e can basically twist around itself, it may cause problems in operation if the belt is wound skewed and not properly.

List of reference numerals:

| | |
|---|---|
| 1 | radiology holding device |
| 2 | attachment device |
| 3 | supporting arm |
| 4 | axle component of 3 |
| 4a | rotation axis |
| 5 | supporting component of 3 |
| 5a | hook |
| 6 | locking device |
| 7 | locking position |
| 8 | actuating mechanism |
| 9 | holding device |
| 10 | hollow section of the axle component 4 |
| 11 | transfer component of 8 |
| 12 | actuating member of 8 |
| 13 | fixing member of 6 |
| 14 | depression of 6 |
| 15 | diameter of the hole circle |
| 16 | diameter of the axle component 4 |
| 17 | biasing device |
| 18 | shield |
| 19 | flexible pull member of 11 |
| 19a | actuation travel of 19 |
| 20 | guide unit |
| 21 | guide roller |
| 22 | deflection sleeve |
| 23 | receiving rail |
| 24 | hooking point |
| 25 | limiting device for the rotational angle |
| 26 | treatment table for patient |
| 27 | protective sleeve |
| 28 | bumper device |
| 29 | hook member |
| 29a | support hook |
| 30 | infusion bag |
| 31 | supporting unit |
| 31a | knob |
| 32 | belt unit |
| 32a | holder |
| 32b | rod |
| 32c | sliding member |
| 32d | bearing |
| 32e | belt |
| 34 | length of 3 |
| 34a | radial distance from 4 |
| 35 | retaining angle of 9 |
| 36 | tube element of 5 |
| 50 | radiology apparatus |
| 51 | X-ray apparatus |
| 52 | MRT apparatus |
| 53 | CT apparatus |
| 54 | radiotherapy apparatus |
| 100 | radiology system |
| 200 | force direction unit |
| 201 | holding part of 200 |

-continued

List of reference numerals:

| | |
|---|---|
| 202 | contour layout of 201 |
| 203 | support part |
| 204 | loop section, node section of 19 |
| 205 | screw unit, receiving unit of 203 |
| 206 | coupling unit |
| 207 | sleeve part of 206 and 203 |
| 208 | fixing unit, screw unit |

The invention claimed is:

1. A radiology holding device, comprising:
an attachment device,
at least one supporting arm pivotally attached to the attachment device, the supporting arm comprising:
at least one axle component pivotally accommodated on the attachment device for pivoting the supporting arm, and
at least one supporting component,
a locking device for locking the supporting arm in at least one locking position,
an actuating mechanism for actuating the locking device,
at least one holding device provided for attachment to the supporting arm, to provide a patient with a holding means,
wherein the actuating mechanism comprises at least one transfer component passing through a hollow section of the axle component.

2. The radiology holding device according to claim 1, wherein the actuating mechanism can be actuated by at least one actuating member.

3. The radiology holding device according to claim 2 wherein the actuating mechanism can be actuated by at least one actuating member, which is disposed radially outwardly of the attachment device.

4. The radiology holding device according to claim 1, wherein the actuating mechanism can be actuated by at least two actuating members that are independent of one another.

5. The radiology holding device according to claim 1, wherein the locking device serves to establish a fixed connection between the supporting arm and the attachment device.

6. The radiology holding device according to claim 1, wherein the locking device comprises at least one fixing member, and wherein the fixing member can be transferred from a locking position to a rotary position, in which the angular position of the supporting arm relative to the attachment device can be changed.

7. The radiology holding device according to claim 6, wherein the locking device comprises at least one fixing member, which engages in at least one click-in element of a plurality of click-in elements, which are configured on the attachment device to enable multiple locking positions.

8. The radiology holding device according to claim 7, wherein the click-in elements are disposed in a circle across a diameter which is larger than the diameter of the axle component.

9. The radiology holding device according to claim 6, comprising at least one biasing device, by means of which the fixing member can be biased in the locking position.

10. The radiology holding device according to claim 1, wherein the axle component of the supporting arm, at least in a central region of the axle component, includes at least one shield extending transverse to the axle component.

11. The radiology holding device according to claim 1, wherein at least one transfer component is passed out of the axle component to at least one region radially outwardly of the axle component.

12. The radiology holding device according to claim 1, wherein the transfer component is guided by at least one guide unit inside the axle component, and passed outwardly out of the axle component from the inside to the outside.

13. The radiology holding device according to claim 1, wherein the at least one transfer component comprises at least one flexible pull member.

14. The radiology holding device according to claim 13, wherein the actuating mechanism includes at least one force direction unit comprising at least one holding part that accommodates the flexible pull member.

15. The radiology holding device according to claim 14, wherein the force direction unit includes at least one support part, which is fixed to the flexible pull member.

16. The radiology holding device according to claim 14, wherein the force direction unit includes at least one support part and the movability of the support part relative to the pull member is limited in at least one direction, and wherein the support part can be propped on the holding part.

17. The radiology holding device according to claim 16, wherein with actuation of an actuating member, a holding part disposed at a larger radial distance than the actuated actuating member, locks movement of the transfer component by means of the support part, so that the operating force substantially acts on the fixing member of the locking device.

18. The radiology holding device according to claim 1, wherein the actuating mechanism comprises at least two transfer components, and wherein the transfer components are interconnected by at least one coupling unit in a force-fit.

19. The radiology holding device according to claim 18, wherein at least one transfer component is deflected by at least one guide roller disposed outwardly of the axle component.

20. The radiology holding device according to claim 18, wherein at least one transfer component is deflected by at least one deflection sleeve.

21. The radiology holding device according to claim 1, wherein at least one transfer component is passed downwardly and axially out of the axle component.

22. The radiology holding device according to claim 1, wherein at least one protective sleeve is disposed on the transfer component, which at least partially envelops the transfer component and protects the transfer component from contamination when in use.

23. The radiology holding device according to claim 1, comprising at least one limiting device for limiting at least one rotational angle.

24. The radiology holding device according to claim 1, wherein the supporting arm comprises at least one bumper device.

25. The radiology holding device according to claim 1, further comprising at least one receiving rail configured with at least one hooking point along the supporting arm.

26. The radiology holding device according to claim 25, wherein the receiving rail comprises a plurality of interconnected hooking points and at least one holding device can be hooked to at least one hooking point of the plurality of interconnected hooking points.

27. The radiology holding device according to claim 25, wherein the holding device comprises at least one hook member for hooking to at least one hooking point.

28. The radiology holding device according to claim 1, wherein the holding device comprises at least one belt unit configured to variably adjust the length of the holding device.

29. The radiology holding device according to claim 28, wherein the belt unit, when ready to use, is supported for rotation about an axis oriented transverse to the horizontal.

30. The radiology holding device according to claim 1 that is at least partially manufactured of materials that cannot be magnetized at all or materials that may be magnetized only with difficulty.

31. A radiology system, comprising:
   at least one radiology apparatus, and
   at least one radiology holding device, comprising:
      an attachment device,
      at least one supporting arm pivotally attached to the attachment device, the supporting arm comprising:
         at least one axle component pivotally accommodated on the attachment device for pivoting the supporting arm, and
         at least one supporting component,
      locking device for locking the supporting arm in at least one locking position,
      an actuating mechanism for actuating the locking device,
      at least one holding device provided for attachment to the supporting arm, to provide a patient with a holding means,
      wherein the actuating mechanism comprises at least one transfer component passing through a hollow section of the axle component.

32. The radiology system according to claim 31, wherein at least one treatment table for patients of a radiology apparatus is at least partially disposed in the operating range of the radiology holding device.

* * * * *